United States Patent
Sevenster

(10) Patent No.: US 11,869,654 B2
(45) Date of Patent: Jan. 9, 2024

(54) PROCESSING MEDICAL IMAGES

(71) Applicant: KONINKLIJKE PHILIPS N.V., Eindhoven (NL)

(72) Inventor: Merlijn Sevenster, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 518 days.

(21) Appl. No.: 17/266,605

(22) PCT Filed: Aug. 6, 2019

(86) PCT No.: PCT/EP2019/071128
§ 371 (c)(1),
(2) Date: Feb. 7, 2021

(87) PCT Pub. No.: WO2020/030643
PCT Pub. Date: Feb. 13, 2020

(65) Prior Publication Data
US 2021/0313047 A1    Oct. 7, 2021

(30) Foreign Application Priority Data
Aug. 7, 2018   (EP) .................................... 18187723

(51) Int. Cl.
G06N 20/00 (2019.01)
G16H 30/40 (2018.01)
(Continued)

(52) U.S. Cl.
CPC ............. G16H 30/40 (2018.01); G06N 20/00 (2019.01); G06T 7/0016 (2013.01); G16H 10/60 (2018.01);
(Continued)

(58) Field of Classification Search
CPC ........ G16H 30/40; G16H 10/60; G16H 30/20; G06N 20/00; G06T 7/0016; G06T 2200/24; G06T 2207/20081
(Continued)

(56) References Cited

U.S. PATENT DOCUMENTS

| 10,970,365 B2 | 4/2021 | Sorenson et al. |
| 2009/0022377 A1 | 1/2009 | Matsue et al. |

(Continued)

FOREIGN PATENT DOCUMENTS

| JP | 2004298209 A | 10/2004 |
| JP | 2010061521 A | 3/2010 |

(Continued)

OTHER PUBLICATIONS

International Search and Written Opinion for International Application No. PCT/EP2019/071128, filed Aug. 6, 2019, 14 pages.

*Primary Examiner* — Charlotte M Baker

(57) ABSTRACT

The invention discloses an apparatus (100) for processing a medical image associated with a subject. The apparatus comprises a clinical information extractor (102) for determining clinical information associated with the medical image; a plurality of image processors (104), each image processor for performing at least one image processing task in respect of the medical image; and an image processing manager (106) for determining, based at least on the determined clinical information associated with the medical image, at least one image processor of the plurality of image processors to perform one or more tasks in respect of the medical image.

14 Claims, 4 Drawing Sheets

(51) Int. Cl.
  *G16H 10/60* (2018.01)
  *G16H 30/20* (2018.01)
  *G06T 7/00* (2017.01)
(52) U.S. Cl.
  CPC ......... *G16H 30/20* (2018.01); *G06T 2200/24* (2013.01); *G06T 2207/20081* (2013.01)
(58) Field of Classification Search
  USPC .......................................................... 382/128
  See application file for complete search history.

(56) References Cited

U.S. PATENT DOCUMENTS

2016/0350480 A1 12/2016 Gerdeman et al.
2016/0350919 A1 12/2016 Steigauf et al.
2017/0357760 A1* 12/2017 Han ........................ G06N 20/00

FOREIGN PATENT DOCUMENTS

WO    2011121457 A1    10/2011
WO    2017129564 A1     8/2017

* cited by examiner

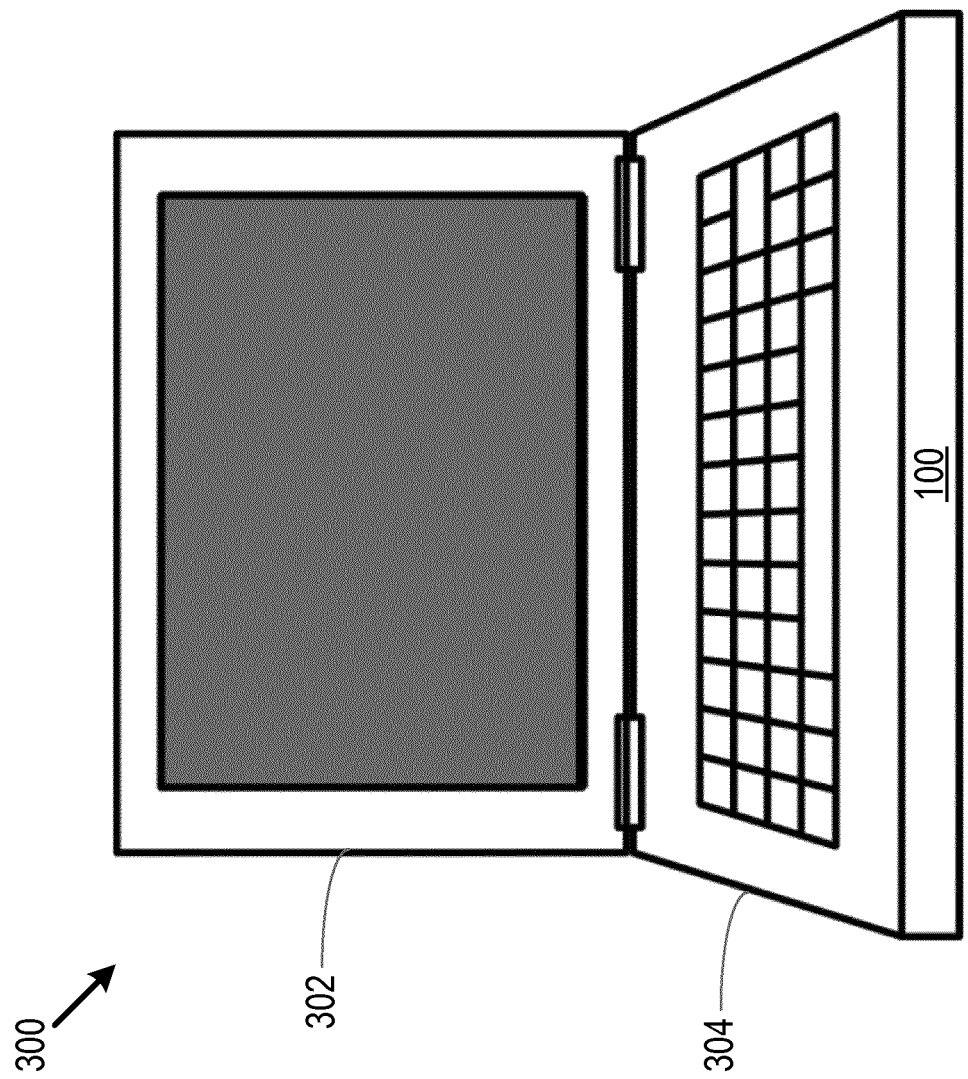

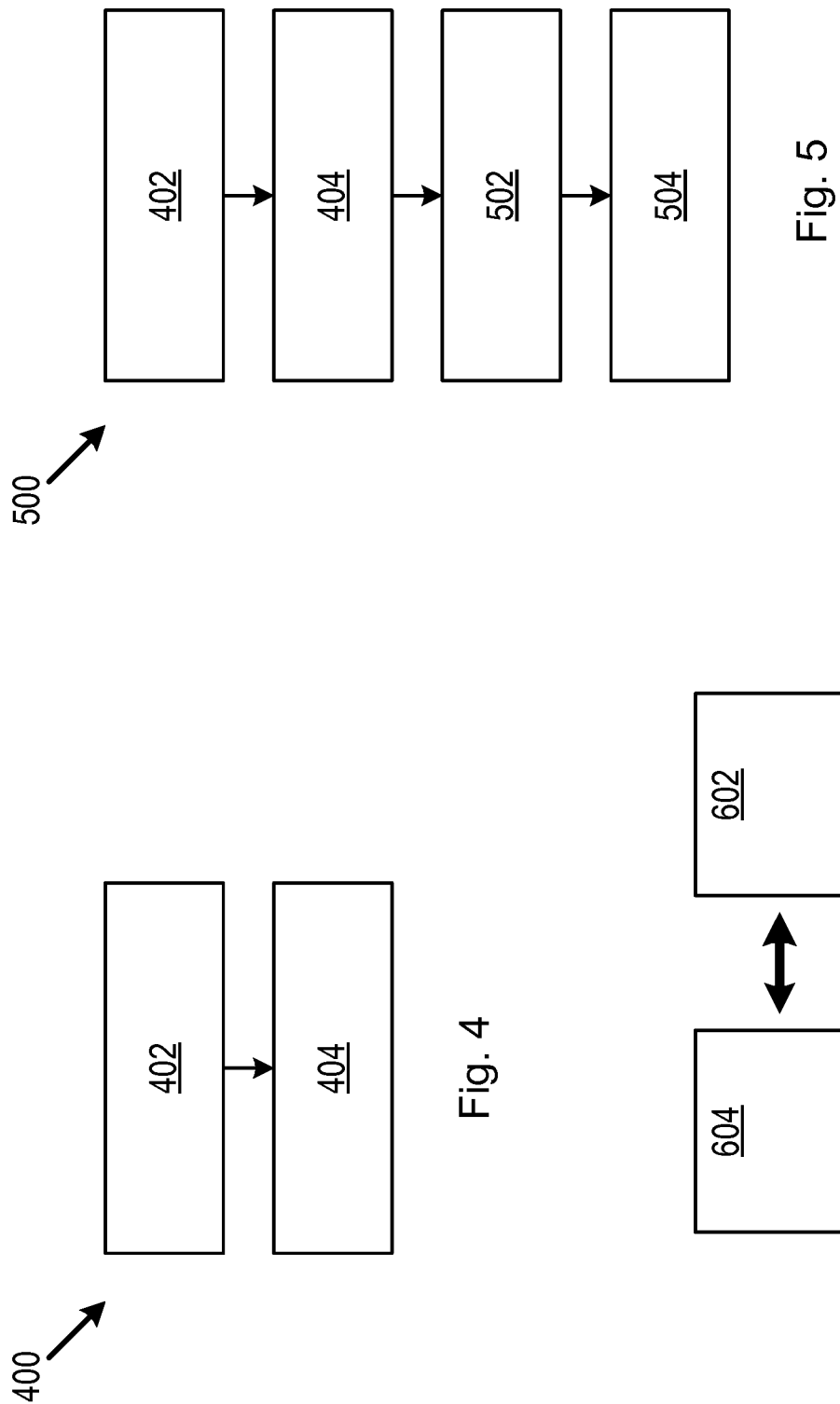

PROCESSING MEDICAL IMAGES

RELATED APPLICATIONS

This application is the U.S. National Phase application under 35 U.S.C. § 371 of International Application No. PCT/EP2019/071128, filed on Aug. 6, 2019, which claims the benefit and priority to European Application No. 18187723.4, filed Aug. 7, 2018, which is incorporated by referenced in its entirety.

FIELD OF THE INVENTION

The invention relates to processing medical images and, more particularly, to processing medical images using one or more of a plurality of image processors. The invention also relates to a method and a computer-readable medium.

BACKGROUND OF THE INVENTION

In the medical field, workflows (also referred to as clinical workflows) can be particularly complex, with different tasks in a workflow intended to be performed by a number of different medical professionals. Over time, workflows may be optimized in terms of quality and efficiency, so that each medical professional responsible for a task in a workflow is capable of performing their relevant task efficiently and effectively so as to avoid introducing delays in respect of other tasks in the workflow.

One example of where workflows can be implemented effectively is in the field of radiology, where radiological examinations can be processed and analyzed by one or more medical professionals (e.g. a radiologist) to interpret the examination and establish some understanding from the radiology examination. While the various tasks can be performed efficiently by the appropriate medical professional, each task can be particularly time-consuming, thereby taking up valuable time of the medical professional.

It is possible to use automated processing mechanisms (e.g. computer processing techniques) to process radiological examinations. For example, computer-implemented image processing techniques might be used to analyze a medical image forming part of a radiological examination in order to perform the processing tasks that would otherwise be performed by a medical professional. For example, computer-implemented techniques incorporating artificial intelligence (AI) mechanisms including, for example, machine learning algorithms, might be used for performing the image processing techniques. However, computer-implemented image processing techniques are not currently at a standard sufficient to replace the work of a skilled medical professional. The experience, insight and expertise of a medical professional can lead to a more effective and accurate outcome when processing a radiological examination, compared to such a processing technique performed by an automated computer-implemented mechanism.

Thus, while the use of automated image processing techniques would be beneficial in saving time of medical professionals, such automated techniques are not that a sufficient standard to enable them to replace the role of the medical professional.

SUMMARY OF THE INVENTION

It has been recognized by the inventors of the present disclosure that, while computer-implemented image processing techniques might not yet be able to replace medical professionals for all analysis and processing of radiological examinations, there might be some processing tasks that can appropriately be performed by an automated mechanism, rather than by a medical professional. Such tasks might, for example, include relatively straightforward processing tasks, tasks which can be checked/confirmed easily by a medical professional and/or tasks for which there is a high likelihood of a particular outcome. Radiological examinations which might be appropriate for processing (e.g. analysis) by a computer-implemented image processor are examinations in which the interpretation or analysis is highly predictable, and does not require significant input from a particular knowledge domain (e.g. input from a highly skilled medical professional).

Therefore, embodiments disclosed herein provide a mechanism by which, for a radiological examination, a determination can be made as to which, if any, processing tasks may be performed by a computer-implemented image processor rather than by a medical professional, based on information relating to the radiological examination.

According to a first aspect, embodiments disclosed herein provide an apparatus for processing a medical image associated with a subject, the apparatus comprising: a clinical information extractor for determining clinical information associated with the medical image; a plurality of image processors, each image processor for performing at least one image processing task in respect of the medical image; and an image processing manager for determining, based at least on the determined clinical information associated with the medical image, at least one image processor of the plurality of image processors to perform one or more tasks in respect of the medical image.

In this way, automated (e.g. computer-implemented) image processors may be used to perform certain, appropriate image processing tasks in respect of the medical image. The appropriateness of a particular task for being performed by an automated image processor is determined based on clinical information associated with the medical image. For example, an image processing task which is expected, to a very high likelihood, to have a particular outcome, may be considered appropriate for automation. More generally, an image processing task might be considered appropriate for automation if, for a plurality of medical images (e.g. radiological examinations), automated execution of the task would be achievable and provide a relevant output. The apparatus enables a workflow to be created that uses computer-implemented image processing mechanisms, thereby reducing the amount of expert human time needed for processing medical images.

In some embodiments, the clinical information extractor may be configured to determine clinical information associated with the medical image from at least one of: the medical image; an electronic health record associated with the subject; a radiology information system; and a database containing a record associated with the subject.

The clinical information may comprise at least one of: a clinical indication of a medical condition associated with the subject; and an indication of an International Classification of Diseases (ICD) identifier of a medical condition associated with the subject.

Each image processor may, in some embodiments, comprise at least one of: an artificial intelligence engine; an image processing engine; a predictive model engine; a machine learning engine; and a statistical analysis engine.

In some embodiments, the apparatus may further comprise a related-image detector for determining whether the medical image is one of a series of related medical images.

The image processing manager may be configured to determine at least one image processor of the plurality of image processors to perform a task in respect of the medical image further based on a determination that the medical image is one of a series of related medical images.

The related-image detector may be configured to compare information associated with the medical image with corresponding information associated with one or more previously-acquired medical images in order to determine whether the medical image is one of a series of related medical images.

In some embodiments, the image processing manager, responsive to determining a plurality of image processors to perform tasks in respect of the medical image, may be configured to determine an order of operation of the determined plurality of image processors.

The image processing manager may be configured to determine an order of operation of the determined plurality of image processors based at least on an output of at least one of the image processors.

In some embodiments, the apparatus may further comprise a user interface for presenting to a user an indication of the determined at least one image processor.

The user interface may, in some embodiments, be further configured to receive a user input to define or adjust a parameter of the determined at least one image processor.

According to a second aspect, embodiments disclosed herein provide a workstation comprising an apparatus as disclosed herein.

According to a third aspect, embodiments disclosed herein provide a method for processing a medical image, comprising: determining clinical information associated with a medical image; and determining, based at least on the determined clinical information associated with the medical image, at least one image processor of a plurality of image processors to perform one or more image processing tasks in respect of the medical image, wherein each image processor is configured to perform at least one image processing task.

In some embodiments, the method may further comprise determining that the medical image is one of a series of related medical images. The determining of the at least one image processor may be based at least on the determination that the medical image is one of a series of related medical images.

In some embodiments, determining at least one image processor may comprise determining a plurality of image processors. The method may further comprise determining an order of operation of the determined plurality of image processors.

According to a fourth aspect, embodiments disclosed herein provide a computer program product comprising a non-transitory computer-readable medium, the computer-readable medium having computer-readable code embodied therein, the computer-readable code being configured such that, on execution by a suitable computer or processor, the computer or processor is caused to perform any of the methods disclosed herein.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 3 is a schematic illustration of a workstation for processing medical image according to various embodiments;

FIG. 4 is a flowchart of an example of a method for processing a medical image;

FIG. 5 is a flowchart of a further example of a method for processing medical image; and FIG. 6 is a simplified illustration of an example of a processor and a computer readable medium.

DETAILED DESCRIPTION OF EMBODIMENTS

Embodiments disclosed herein provide a mechanism by which data relating to a medical image of a radiological examination can be obtained and used to determine whether or not any image processing tasks to be performed in respect of the medical image can be performed by a computer-implemented, or automated, image processing mechanism, rather than by a human medical professional, such as a radiologist. Currently, some image processing tasks are relatively straightforward, and can be performed at lower cost and with low variability by technical support staff rather than by radiologists. It is envisaged that some image processing tasks (e.g. those relatively straightforward tasks) could suitably be performed by a computer-implemented image processor, thereby reducing the number of man-hours that are to be spent reviewing and analyzing radiological examinations.

Figure 1:
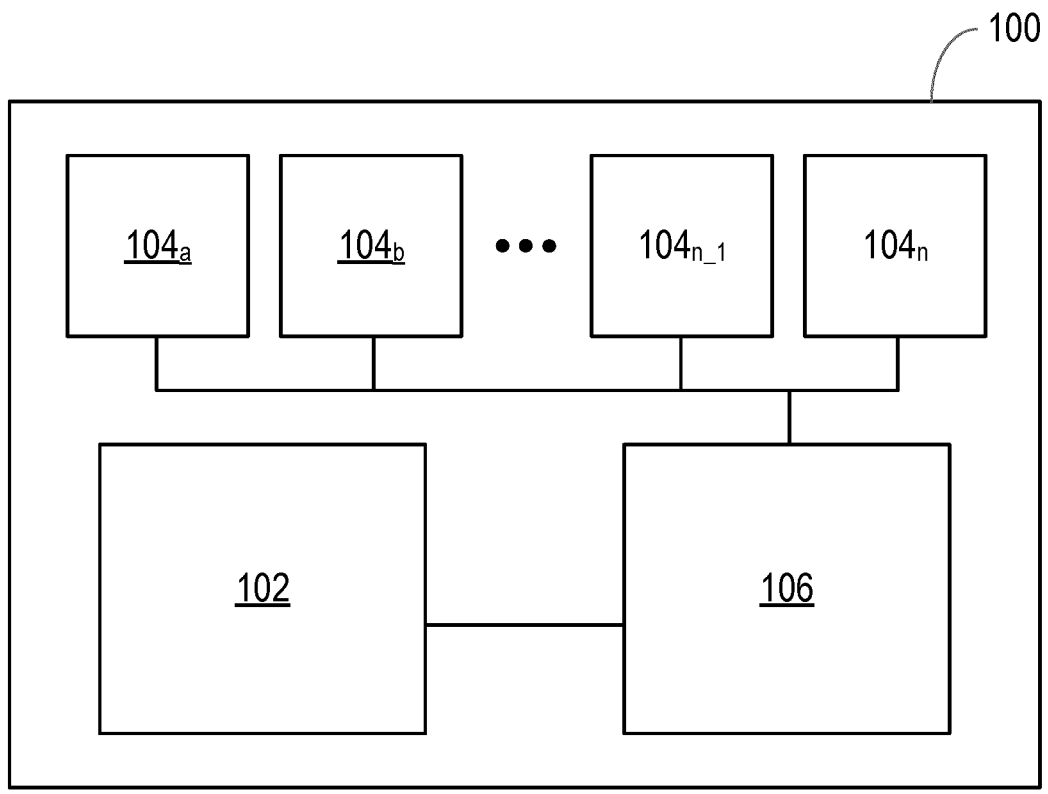
FIG. 1 is a schematic illustration of an example of an apparatus for processing a medical image according to various embodiments.

According to a first aspect, various embodiments disclosed herein provide an apparatus for processing a medical image associated with a subject. FIG. 1 is a simplified schematic illustration of an example of such an apparatus 100. The medical image may form part of a radiological examination (also referred to as a radiological examination study or a medical imaging study). In some embodiments, a radiological examination may comprise just a medical image while, in other embodiments, a radiological examination may comprise one or more medical images (e.g. a stack or series of medical images) in addition to other information, such as text, data included in one or more data fields, annotations or the like. The medical image may be acquired using any medical imaging modality or technique including, for example, x-ray imaging, magnetic resonance imaging (MRI), ultrasonography or ultrasound, positron emission tomography (PET), computed tomography (CT) and single-photon emission computed tomography (SPECT). Other imaging modalities that are familiar to those skilled in the art may also be used to acquire the medical image.

As used herein, the term "subject" is intended to refer to any human or animal in respect of whom a medical image can be acquired, for example using one of the above-mentioned techniques. The subject may, for example, comprise a patient of a medical facility in respect of whom a medical image has been acquired, for example for investigative, diagnostic or prognostic purposes.

The apparatus 100 comprises a clinical information extractor 102 for determining clinical information associated with the medical image. The clinical information extractor 102 may, for example, comprise a module, an engine or a processor configured to obtain clinical information relating to the medical image. In some embodiments, the clinical information extractor 102 may obtain or determine clinical information associated with the medical image from the medical image itself. For example, the medical image may include information indicating the nature of the medical condition leading to the acquisition of the medical image, an indication of the body part and/or the anatomical object captured in the medical image, information identifying the subject (e.g. the subject's name, date of birth, patient identification number, medical record number, medical imaging study accession ID, and the like) and/or a clinical indication of the relevant medical condition (e.g. a medical condition from which the subject is suffering or suspected of suffering, or the medical condition forming the subject of the medical imaging study). The clinical information may, in some embodiments, be referred to as an exam indication, which comprises an indication of the type and/or nature of the medical imaging examination relevant to the medical image.

In some embodiments, the clinical information or exam indication may comprise a code (e.g. a clinical indication code) indicative of the type of medical imaging study and/or a medical condition relevant to the medical image. For example, the clinical information may comprise a word or code from a defined wordlist (e.g. a lexicon) or from a defined hierarchy (e.g. an ontology). In some embodiments, the clinical information may comprise a code as defined according to the International Classification of Disease (ICD). In some cases, clinical information (e.g. a clinical indication) may be associated with and/or added to a medical image when the medical images captured by a medical imaging system. Such information may be provided to the medical image automatically by the medical imaging system or manually by an operator of such a system or a medical professional.

In some embodiments, a clinical indication code may be refined using other clinical information obtained or determined by the clinical information extractor 102. For example, the clinical indication code may be refined using information relating to the imaging modality used to capture the medical image and/or an indication of the body part or anatomical object of the medical imaging study. Each unique combination (e.g. the combination of each imaging modality with each body part or anatomical object) may be mapped to code in a set of clinical indication codes. For example, if the imaging modality used to capture the medical image is identified as a low-dose CT scan, and the body part of the imaging study is identified as the chest, then it may be determined that a relevant clinical indication code is a code corresponding to a "lung nodule screening indication".

The clinical information to be extracted by the clinical information extractor 102 may, in some embodiments, comprise an indication of a "clinical question" of the medical imaging study. A clinical question may comprise an indication of the relevance of a medical image or medical imaging study, and may provide an indication of why the medical image has been captured and/or what information is intended to be determined from the medical image. In some examples, the clinical question and/or a clinical indication code may be entered by a medical professional, such as a radiologist. The clinical question and/or the clinical indication code may be selected from a list (e.g. a drop-down list) of example clinical questions and/or clinical indications. In other examples, the clinical question and/or the clinical indication code may be entered as free text by a user. In one example, natural language processing techniques may be applied to interpret information included in the clinical question, such as understanding and expanding abbreviations, extracting concepts included in the clinical question, and determining the scope of negation of expressions included in the clinical question. Un-negated concepts included in the clinical question may be mapped to one or more codes (e.g. clinical indication codes) using an ad hoc mapping technique or using rules or reasoning patterns associated with or forming part of an ontology, such as a medical ontology (e.g. SNOMED).

While the clinical information may, in some examples, be obtained or determined from the medical image itself, the clinical information may, in other examples, be obtained from other sources. Thus, the clinical information extractor 102 may be configured to determine clinical information associated with the medical image from at least one of: the medical image; an electronic health record associated with the subject; a radiology information system (RIS); and a database containing a record associated with the subject. A subject's electronic health record may, for example, be stored and made available via a computer system or via a shared computing network. Clinical information extracted from an electronic health record of the subject may comprise an indication of any medical conditions from which the subject is suffering or has previously suffered, an indication of any previous medical imaging studies relevant to the subject and/or an indication of any medical images that have previously been captured in respect of the subject. Thus, from the subject's electronic health record, it may be possible to determine whether or not the medical condition for which the medical image has been captured is a new condition, subject or an ongoing or recurring issue. A radiology information system may include details of, and medical images associated with, any previous radiological examination studies that have been carried out in respect of the subject. Therefore, it may be possible to determine from the RIS whether a particular medical image relates to a new medical condition or to a previously-identified or recurring medical condition. Information associated with the subject may be stored in one or more records in a database, and clinical information associated with medical image may be acquired from such records or databases. In other examples, clinical information associated with the medical image may be obtained or determined from another source.

The clinical information may comprise at least one of: a clinical indication of a medical condition associated with the subject; and an indication of an International Classification of Diseases (ICD) identifier of a medical condition associated with the subject. A medical condition associated with the subject may, for example, comprise a medical condition from which the subject is suffering or a medical condition from which the subject is expected to be suffering. For example, the subject may experience symptoms suggesting that he or she is suffering from a particular medical condition and, as a result, a medical professional (e.g. a doctor) may arrange for a medical imaging scan to be captured for further investigation. In other examples, the clinical information may comprise information or data of another type.

The apparatus 100 further comprises a plurality of image processors 104, each image processor 104 for performing at least one image processing task in respect of the medical image. In the example shown in FIG. 1, the apparatus 100 includes the image processors 104$_a$, 104$_b$ . . . 104$_{n-1}$, 104$_a$, where n is the number of image processors. Each image processor 104 may, for example, comprise circuitry or an engine configured to perform one or more image processing tasks. In some examples, each image processor 104 may comprise at least one of: an artificial intelligence engine; an image processing engine; a predictive model engine; a machine learning engine; and a statistical analysis engine. A machine learning engine may employ machine learning techniques including, for example, decision tree algorithms, artificial neural networks, deep learning neural networks, support vector machines, Bayesian networks, and the like, which will be familiar to those skilled in the field of machine learning.

The image processors 104 may be configured to perform any image processing task, in particular, an image processing task relevant to the field of medical image analysis. In some examples, an image processor 104 may be configured to detect the presence of a defined entity in the medical image. For example, an image processor may be configured to detect the presence of a lesion, a tumor, an abnormality, a fracture, a tear, or some other feature visible or detectable in the medical image. In some examples, an image processor 104 may be configured to locate or determine the location of (e.g. identify the location, for example using a coordinate system) a defined entity (e.g. a lesion, tumor, abnormality etc.) in the medical image. An image processor 104 may, in some examples, be configured to determine the boundaries of a defined entity or of a detected entity. For example, once a defined entity has been detected by one of the image processors 104, an image processor (e.g. the same image processor that performed the detection or a different one of the image processors) may locate and/or detect one or more boundaries of the defined entity. In some examples, an image processor 104 may determine at least one size, dimension or volume of a defined entity or of a detected entity. For example, a dimension may include a length, a width, a height or a depth. This may be referred to as quantification of the defined entity. A volume of the defined entity may be determined or estimated using one or more of the determined dimensions and/or one or more other methods. In some examples, an image processor 104 may be configured to perform a segmentation task (e.g. lesion segmentation) in respect of a defined entity in the medical image. For example, the defined entity (e.g. a lesion) may be segmented, delineated or visually separated from other parts of the medical image. An image processor 104 may, in some examples, be configured to determine a change in one or more characteristics or features of the medical image over time (e.g. as compared to a previously-captured medical image). An image processor 104 may be configured to determine a diagnosis of a defined entity. For example, the image processor 104 may be configured to recognize or determine a feature present in the medical image that is representative of a particular medical condition. In making such a determination, an output of the image processor may be combined with information obtained from another source, such as an electronic health record associated with the subject. In some embodiments, an image processor 104 may be configured to determine a treatment option based on a detected entity. Such a determination may, for example, be made using a lookup table or database, based on the nature of the defined entity, and/or using a predictive model (e.g. a machine learning model).

In some examples, an image processor 104 may be configured to perform multiple image processing tasks, such as those image processing tasks discussed above.

In any of the above examples, a "defined entity" may be an entity defined by a user or an entity selected automatically (e.g. using a recognition model or machine learnt predictive model). For example, depending on the nature of the medical imaging study, and the nature of the medical image being processed, the image processor 104 may determine the defined entity to be detected, measured, diagnosed, and so on. In other examples, an image processor 104 may be configured to perform a particular image processing task in respect of a particular defined entity. For example, an image processor 104 may configured only to detect a fracture in a bone.

The apparatus 100 further comprises an image processing manager 106 for determining, based at least on the determined clinical information associated with the medical image, at least one image processor 104 of the plurality of image processors to perform one or more tasks in respect of the medical image. The image processing manager 106 may comprise processing circuitry (e.g. a processor) or controller. For example, the image processing manager 106 may comprise a processor configured to execute a set of instructions. The image processing manager 106 may, in some embodiments, use one or more rules to decide which, if any, of the image processors 104 should be implemented in order to perform a task in respect of the medical image. The determination made by the image processing manager 106 is based on the determined clinical information associated with the medical image. In this way, the image processing manager 106 is able to implement an appropriate image processor 104 in appropriate cases. For example, the image processing manager 106 may determine that an image processor 104 configured to detect a bone fracture may be implemented if there is a high certainty of the outcome of such a determination. For example, clinical information extracted from an electronic health record for a subject may indicate that there is an extremely low likelihood that a bone is fractured, and an x-ray scan may have been performed in order to confirm this. Rather than a radiologist spending time reviewing the medical image (i.e. the x-ray scan image), the image processing manager 106 may determine a particular image processor 104 should be implemented to perform the processing of the x-ray scan image. In other examples, the image processing manager 106 may determine that a particular image processor 104 should be implemented when the processing task to be performed is relatively straightforward and/or where the outcome of the image processing task is not of particular importance. In other examples, an image processor 104 may be implemented when it is known that the output of the image processor will, at some point, be checked by a medical professional.

If it is determined by the image processing manager 106 that none of the image processors 104 can appropriately be implemented to perform an image processing task in respect of the medical image, then no image processors will be implemented. In such a scenario, the image processing manager 106 may generate and/or output such a determination for presentation to a user. In this way, a user (e.g. a medical professional) will know that human input is required and, therefore, resources can be provided appropriately to enable the workflow to be completed. In cases where the image processing manager 106 determines that one or more image processors 104 be used to perform one or more image processing tasks in respect of the medical image, then such a determination may be output for presentation to a user. In some examples, the image processing manager 106 may control one or more of the image processors 104 to perform the tasks.

Figure 2:
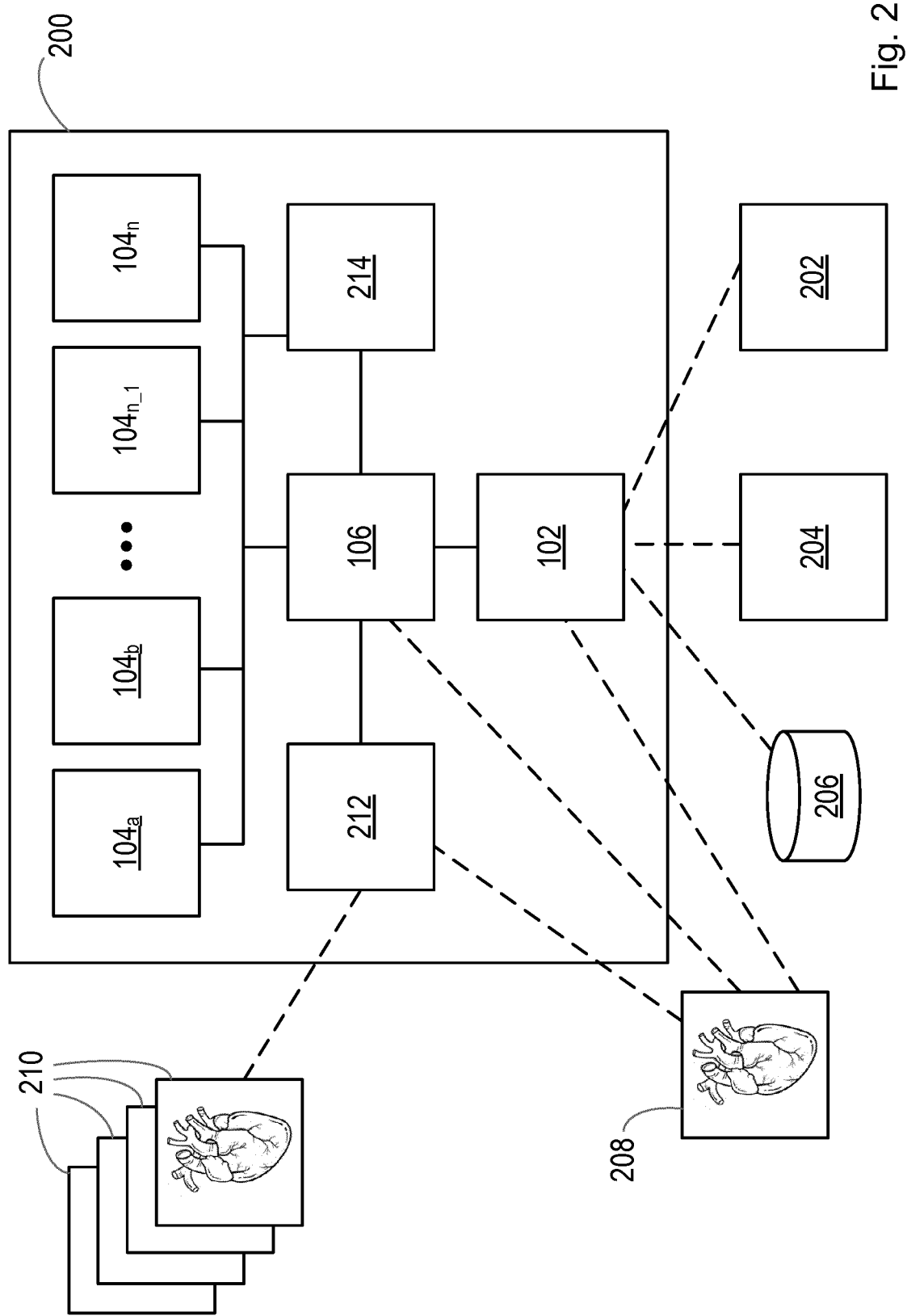
FIG. 2 is a schematic illustration of a further example of an apparatus for processing a medical image according to various embodiments.

FIG. 2 is a simplified schematic of a further example of an apparatus 200 for processing a medical image associated with the subject. The apparatus 200 may include the clinical information extractor 102, the plurality of image processors 104 and/or the image processing manager 106 as described herein. An electronic health record 202, a radiology information system (RIS) 204 and a database 206 are also shown in FIG. 2, each being in communication with the clinical information extractor 102. FIG. 2 also shows the medical image 208 associated with the subject, and one or more related medical images 210. As discussed above, the clinical information extractor 102, may extract or determine clinical information from one or more of the electronic health record 202, the RIS 204, the database 206 and the medical image 208.

The apparatus 200 may further comprise a related-image detector 212 for determining whether the medical image 208 is one of a series of related medical images 210. The image processing manager 106 may be configured to determine at least one image processor 104 of the plurality of image processors to perform a task in respect of the medical image 208 further based on a determination that the medical image is one of a series of related medical images 210. The medical image 208 may be one of a series of related medical images 210 if, for example, the medical image is captured as part of a follow-up examination. Such an examination may be relevant for a subject who is receiving ongoing treatment for a particular medical condition. For example, a subject may have had one or more previous medical imaging scans in order to investigate a particular medical condition. It may be appropriate to arrange for a series of medical images 210 to be captured over a period of time so that the progression of the medical condition can be examined. Such previously-acquired medical images may be stored in a storage medium accessible by components of the apparatus 100, 200, such as the image processing manager 106. In some examples, it might be expected that a medical image forming part of a series of related medical images 210 will be similar to one or more of the previously-captured related images (e.g. if there has been relatively little development of the medical condition between capturing the two images). In such cases, it may be appropriate to use one or more image processors 104 to perform image processing tasks in respect of the medical image 208 (i.e. a follow-up image) since there is a high likelihood that the outcome of the image processing will be as expected (e.g. unchanged from the previous medical image in the series of related images 210). Furthermore, since only a relatively little image processing may be necessary in respect of a follow-up image, it may be more efficient for an image processor 104 to be implemented in the workflow rather than having a medical professional perform the image processing manually.

The related-image detector 212 may determine whether or not the medical image 208 is one of a series of related medical images 210 using a variety of techniques. For example, the related-image detector 212 may implement a rule-based mechanism by which the medical image 208 may be determined to be a follow-up image in the series of related medical images 210 if one or more defined rules or criteria are met. In some examples, the related-image detector 212 may implement a statistical analysis mechanism by which the medical image 208 is considered to be a follow-up image in the series of related medical images 210 if a statistical likelihood exceeds a threshold (e.g. if the medical image 208 is statistically similar to the series of related medical images 210). In some examples, the related-image detector 212 may implement a machine learning model or predictive model by which a determination is made based on an understanding obtained from a set of learning data.

In some embodiments, the related-image detector 212 may use information from the medical image 208 and from the series of medical images 210 in order to determine whether the medical image forms part of the series of related medical images 210. For example, information used to make such a determination may include one or more of the following: information relating to the imaging modality used to capture the medical image; information relating to a body part or anatomical object in the medical image; information indicating a time interval between each image in the series of related medical images 210 and/or a time interval between capturing the medical image 208 and on or more of the series of related images; information relating to ordering codes and/or billing codes associated with the subject and/or with the medical images 208, 210; and information included in a report accompanying or associated with one or more of the images in the series of related medical images 210. An ordering code is a code assigned or allocated by a referring physician when the medical study is entered in medical computing system. The ordering code may provide a high-level description of the study, including, for example, an imaging modality type, the anatomy to be imaged, and so on. A billing code is a code representing the type of study that was actually performed. This may, for example, be the study for which a medical facility can charge for.

In one example, if it is determined that each of the images in the series of related medical images 210 was captured around 3 months after the previous image, and it is determined that the medical image 208 was captured around 3 months after the previous medical image, then it may be determined that the latest medical image forms part of the series of related medical images 210. In some examples, the medical image 208 may be determined to be part of the series of related medical images 210 if a threshold number of criteria are met (e.g. if it is determined that the imaging modality and body part are the same, and that the time interval between capturing subsequent medical images is constant).

Thus, in some embodiments, the related-image detector 212 may be configured to compare information associated with the medical image 208 with corresponding information associated with one or more previously-acquired medical images in order to determine whether the medical image is one of a series of related medical images 210.

If the related-image detector 212 determines that the medical image 208 is one of a series of related medical images 210, then the same or similar image processors 104 that were applied in respect of the series of medical images may be applied in respect of the medical image 208. For example, the image processing manager 106 may determine which image processors 104 were used in processing the medical images 210, and arrange for the same image processors to be used in in processing the medical image 208.

While, in some embodiments, the image processing manager 106 may determine just one image processor 104 to perform an image processing task in respect of the medical image 208, in other embodiments, the image processing manager may determine multiple image processors to determine multiple image processing tasks. For example, the image processing manager 106 may determine that a first image processor (e.g. $104_a$) is to perform a first image processing task (e.g. detecting a defined entity, such as a tumor, in the medical image 208) and a second image processor is to perform a second image processing task (e.g. determining a volume of the defined entity/tumor). Thus, according to some embodiments, the image processing manager 106, responsive to determining a plurality of image processors 104 to perform tasks in respect of the medical image 208, may be configured to determine an order of operation of the determined plurality of image processors. Determining the order of operation of the plurality of image processors 104 is helpful for incorporating the various image processing tasks into a workflow. In this way, a medical professional may be able to determine exactly which image processing tasks are being performed by image processors 104 and which are to be performed by human users (e.g. radiologists). A medical professional may also be able to determine the order in which each image processing task is to be performed. The image processors 104 determined by the image processing manager 106, and/or the determined order in which the image processing tasks are to be performed may be delivered for presentation to a user.

In some embodiments, one or more of the image processors 104 may be provided by a user (e.g. a medical professional). For example, a user may define one or more parameters of the image processor, and/or may configure the image processor to provide an intended output. In other embodiments, however, the output from one image processor 104 may be used as an input for another image processor. Thus, according to some embodiments, the image processing manager 106 may be configured to determine an order of operation of the determined plurality of image processors 104 based at least on an output of at least one of the image processors. For example, if a first image processor 104 determines that a defined entity is present in the medical image 208, then the image processing manager 106 may determine that another image processor is to perform a further image processing task. In some examples, the output from one image processor 104 may determine which image processor is used to perform the next image processing task.

In embodiments in which multiple image processors 104 are determined/chosen to perform image processing tasks, the image processing manager 106 may, in some examples, determine the sequential trajectory or route through the various image processors. The order in which the image processors 104 are to be implemented may be determined based on a known order or sequence (e.g. if a particularly effective sequence of image processing tasks is known) or based on the output of one or more of the image processors, as noted above.

In some embodiments, the apparatus 200 may further comprise a user interface 214 for presenting to a user an indication of the determined at least one image processor 104. For example, the user interface 214 may display to a user an indication of representation of the image processor(s) 104 chosen to perform one or more image processing tasks. In this way, the user is able to monitor the workflow and monitor the progress of the various image processing tasks forming part of the workflow.

The user interface 214, in addition to presenting information to a user, may enable a user to enter information. The user interface 214 may, for example, be capable of receiving a user input via a user input device, such as a keyboard, a touch screen, a touchpad, a mouse, a microphone (e.g. via a voice input) or some other means that will be familiar to those skilled in the art. In some embodiments, the user interface 214 may be further configured to receive a user input to define or adjust a parameter of the determined at least one image processor 104. For example, a user (e.g. a medical professional such as a radiologist) may define one or more parameters of one or more user interfaces 104, and/or may adjust one or more previously-defined parameters. In this way, a user is able to choose how each image processor 104 operates how each image processor performs its corresponding image processing task(s). For example, a user may wish to increase a sensitivity of an image processor 104 configured to detect a particular defined entity (e.g. a lesion), such that the image processor has a lower threshold for detecting the particular defined entity.

In some embodiments, the user interface 214 may present the intended order of operation of the user interfaces 104 graphically, for example in the form of a series of blocks in a chart. As the workflow progresses (e.g. as each image processor 104 performs its task(s)), the appearance of each block the change (e.g. a block corresponding to a particular image processor may change color once the image processor has performed its task or tasks). In some embodiments, a user may navigate through the graphical representation of the image processors 104, for example to allow him or her to select one of the image processors in order to adjust a parameter.

In some examples, the image processing manager 106 may determine that, at a particular point in a workflow, multiple image processing tasks can be performed by multiple image processors 104. In such an example, the user interface 214 may present the various options to a user, so that the user may select which of the image processors is to perform a task and/or an order in which the image processors are to perform the various tasks. The determination of which processor 104 should be implemented at such a branching point in a workflow may be based in part on an output from one or more of the other image processors and/or an input or decision provided by a user.

The image processing manager 106 may, in some embodiments, determine that no further image processing tasks are to be performed using the image processors 104 and/or that all of the intended image processing for a medical image 208 has been performed. It is determined that no further tasks are to be performed by the image processors 104, then a report may be generated for presentation to a user/medical professional. The report may be generated by a processor associated with the apparatus 100, 200 and, in some embodiments, the report may be generated using the image processing manager 106. In some examples, the apparatus 200 may further comprise a report generator (not shown) for generating a report based on an output of one or more image processors 104. The report may, in some embodiments, comprise a preliminary report which can be provided to a medical professional for review. In some examples, a report may be created in machine understandable language or human understandable language, and the report may be integrated into a diagnostic radiology report. Thus, at least part of a report generated using the apparatus 100, 200 may be combined with at least part of a report generated by a human (e.g. a radiologist) so as to create a full diagnostic report.

Elements of the apparatus 100, 200, such as the user interface 214, may be incorporated into or integrated with a computing system or software, such as a Picture Archiving and Communication System (PACS) client. In this way, once all of the image processing tasks have been performed by the image processors 104, outputs from the image processors, or a report generated by the apparatus 100, 200, may be provided to a PACS reporting engine and/or to a PACS interpretation/diagnosis engine for further processing. In other examples, elements of the apparatus 100, 200 may be incorporated into a stand-alone application (e.g. a software application) that can be executed on a computing system.

In some embodiments, the apparatus 100, 200 may comprise or be incorporated into a computing device, such as a desktop computer, a laptop computer, a tablet computer, a smart phone, a wearable computing device and/or a distributed computing system (e.g. in a cloud computing environment).

According to a second aspect, various embodiments disclosed herein provide a workstation. In some examples, the apparatus 100, 200 may comprise or be incorporated into a workstation. FIG. 3 is a simplified schematic of an example of a workstation 300. The workstation 300 may comprise the apparatus 100, 200 as disclosed herein. The workstation 300 may also comprise a display screen 302 and/or a user input device 304, such as a keyboard.

According to a third aspect, various embodiments disclosed herein provide a method for processing medical image. FIG. 4 is a flowchart of an example of a method 400 for processing medical image (e.g. the medical image 208). The method 400 comprises, at step 402, determining clinical information associated with a medical image. The medical image may, for example, comprise an image 208 discussed herein. The clinical information determined in step 402 may, in some embodiments, be determined using the clinical information extractor 102 discussed herein. At step 404, the method 400 comprises determining, based at least on the determined clinical information associated with the medical image, at least one image processor of a plurality of image processors to perform one or more image processing tasks in respect of the medical image, wherein each image processor is configured to perform at least one image processing task. The image processors may comprise the image processors 104 discussed herein. Thus, the method 400 may be performed by the apparatus 100, 200 and/or may be performed using the workstation 300.

Processing a medical image using the method 400 may help to reduce the amount of time of a medical professional (e.g. a radiologist) needed to perform in image processing tasks in respect of the medical image as part of a workflow. As such, the processing of the medical image, and the progression through the workflow, may be improved and/or optimized.

FIG. 5 is a flowchart of a further example of a method 500 for processing a medical image. The method 500 may include steps of the method 400 discussed above. In some embodiments, the method 500 may further comprise, at step 502, determining that the medical image is one of a series of related medical images. Such a determination may be made using techniques discussed herein. Determining of the at least one image processor (step 404) may be based at least on the determination that the medical image is one of a series of related medical images. Thus, if it is determined that the medical image forms part of a series of related medical images, then it may be determined that some image processing tasks can suitably be performed using the image processors, rather than a human (e.g. a medical professional). Accordingly, such a determination is made, then one or more image processors may be implemented into the workflow.

In some embodiments, determining at least one image processor (step 404) may comprise determining a plurality of image processors. In other words, it may be determined that multiple image processors may be used for performing multiple image processing tasks in respect of the medical image. In such cases, the method 500 may further comprise, at step 504, determining an order of operation of the determined plurality of image processors. The determination of one or more image processors and/or the determined order of operation of the plurality of image processors may be provided for presentation to a user, for example using the user interface 214 discussed herein.

According to a fourth aspect, various embodiments disclosed herein provide a computer program product. FIG. 6 is a simplified schematic of an example of a processor 602 and a computer-readable medium 604. According to some embodiments, a computer program product comprises a non-transitory computer-readable medium 604, the computer-readable medium having computer-readable code embodied therein, the computer-readable code being configured such that, on execution by a suitable computer or processor 602, the computer or processor is caused to perform steps of the methods 400, 500 disclosed herein. In some embodiments, the processor 602 may comprise, function as part of, or operate in association with the image processing manager 106 disclosed herein. Similarly, one or more of the plurality of image processors 104 may form part of the processor 602.

The processor 602 can comprise one or more processors, processing units, multi-core processors or modules that are configured or programmed to control elements of the apparatus 100, 200 in the manner described herein. In particular implementations, the processor 602 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for processing a medical image associated with a subject, the apparatus comprising:
   a clinical information extractor for determining clinical information associated with the medical image;
   a plurality of image processors, each image processor for performing at least one image processing task in respect of the medical image, and each image processor comprising of at least one of: an artificial intelligence engine; a privacy model engine; a machine learning engine; and a statistical analysis engine; and
   an image processing manager for determining, based at least on the determined clinical information associated with the medical image, at least one image processor of the plurality of image processors to perform one or more tasks in respect of the medical image.

2. An apparatus according to claim 1, wherein the clinical information extractor is configured to determine clinical information associated with the medical image from at least one of: the medical image; an electronic health record associated with the subject; a radiology information system; and a database containing a record associated with the subject.

3. An apparatus according to claim 1, wherein the clinical information comprises at least one of: a clinical indication of a medical condition associated with the subject; and an indication of an International Classification of Diseases, ICD, identifier of a medical condition associated with the subject.

4. A workstation comprising an apparatus according to claim 1.

5. An apparatus according to claim 1, further comprising:
   a related-image detector for determining whether the medical image is one of a series of related medical images;
   wherein the image processing managers is configured to determine at least one image processor of the plurality of image processors to perform a task in respect of the medical image further based on a determination that the medical image is one of a series of related medical images.

6. An apparatus according to claim 5, wherein the related-image detector is configured to compare information associated with the medical image with corresponding information associated with one or more previously-acquired medical images in order to determine whether the medical image is one of a series of related medical images.

7. An apparatus according to claim 1, wherein the image processing manager, responsive to determining a plurality of image processors to perform tasks in respect of the medical image, is configured to determine an order of operation of the determined plurality of image processors.

8. An apparatus according to claim 7, wherein the image processing manager is configured to determine an order of operation of the determined plurality of image processors based at least on an output of at least one of the image processors.

9. An apparatus according to claim 1, further comprising:
   a user interface for presenting to a user an indication of the determined at least one image processor.

10. An apparatus according to claim 9, wherein the user interface is further configured to receive a user input to define or adjust a parameter of the determined at least one image processor.

11. A method for processing a medical image, comprising:
    determining, using a processor, clinical information associated with a medical image; and
    determining, using a processor, based at least on the determined clinical information associated with the medical image, at least one computer-implemented image processor of a plurality of computer-implemented image processors to perform one or more image processing tasks in respect of the medical image, wherein each computer-implemented image processor is configured to perform at least one image processing task, and wherein each image processor comprises of at least one of: an artificial intelligence engine; a predictive model engine; a machine learning engine; and a statistical analysis engine.

12. A computer program product comprising a non-transitory computer-readable medium, the computer-readable medium having computer-readable code embodied therein, the computer-readable code being configured such that, on execution by a suitable computer or processor, the computer or processor is caused to perform the method of claim 11.

13. A method according to claim 11, further comprising:
    determining, using a processor, that the medical image is one of a series of related medical images;
    wherein said determining of the at least one computer-implemented image processor is based at least on the determination that the medical image is one of a series of related medical images.

14. A method according to claim 11, wherein said determining at least one computer-implemented image processor comprises determining a plurality of computer-implemented image processors, the method further comprising:
    determining an order of operation of the determined plurality of computer-implemented image processors.

* * * * *